US008267875B2

(12) United States Patent
Chau et al.

(10) Patent No.: US 8,267,875 B2
(45) Date of Patent: Sep. 18, 2012

(54) METHOD AND SYSTEM OF SEGMENTATION AND TIME DURATION ANALYSIS OF DUAL-AXIS SWALLOWING ACCELEROMETRY SIGNALS

(76) Inventors: Tom Chau, Toronto (CA); Ervin Sejdic, Toronto (CA)

( * ) Notice: Subject to any disclaimer, the term of this patent is extended or adjusted under 35 U.S.C. 154(b) by 401 days.

(21) Appl. No.: 12/606,797

(22) Filed: Oct. 27, 2009

(65) Prior Publication Data

US 2010/0160833 A1 Jun. 24, 2010

Related U.S. Application Data

(60) Provisional application No. 61/109,223, filed on Oct. 29, 2008.

(51) Int. Cl.
*A61B 5/103* (2006.01)
*A61B 5/117* (2006.01)
(52) U.S. Cl. ........ 600/593; 600/561; 600/586; 600/587; 600/589; 600/590
(58) Field of Classification Search .................. 600/561, 600/586–593; 607/39–40, 62, 72, 118
See application file for complete search history.

(56) References Cited

U.S. PATENT DOCUMENTS

| 5,263,491 | A | * | 11/1993 | Thornton | 600/587 |
|---|---|---|---|---|---|
| 5,274,548 | A | * | 12/1993 | Bernard et al. | 600/500 |
| 2005/0283096 | A1 | * | 12/2005 | Chau et al. | 600/593 |
| 2007/0238920 | A1 | * | 10/2007 | Sato et al. | 600/102 |
| 2008/0306373 | A1 | * | 12/2008 | Kandori et al. | 600/407 |
| 2009/0030346 | A1 | * | 1/2009 | Kojima et al. | 600/590 |

OTHER PUBLICATIONS

Article to Das, Reody and Narayanan, entitled "Hybrid fuzzy logic committee neural networks for recognition of swallow acceleration signals", Computer Methods and Programs in Biomedicine, 64 (2001) 87-99, Elsevier Science ireland Ltd.*

* cited by examiner

*Primary Examiner* — Rene Towa
(74) *Attorney, Agent, or Firm* — Gordon Thomson

(57) ABSTRACT

The proposed invention is a method and system for the segmentation of dual-axis accelerometry signals for the purposed of identifying problematic swallowing events. The method and system employ a sensor, a data collection means including an algorithm for the analysis of the data. The proposed invention considers the stochastic properties of swallowing signals in both directions, A-P and S-I to extract events associated with swallowing. A segmentation algorithm may be applied to the signals to establish the time duration of swallows and swallows may be classified with respect to gender, body mass index, age or types of swallow.

11 Claims, 9 Drawing Sheets

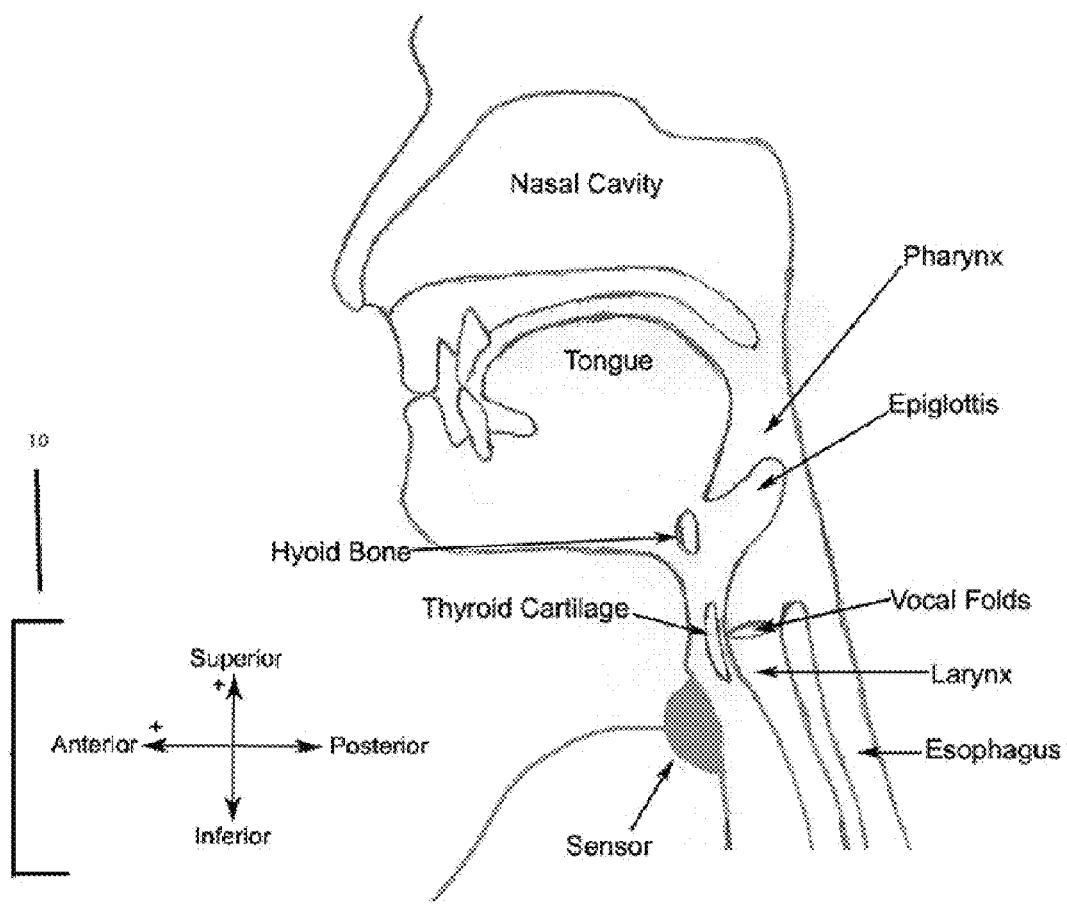

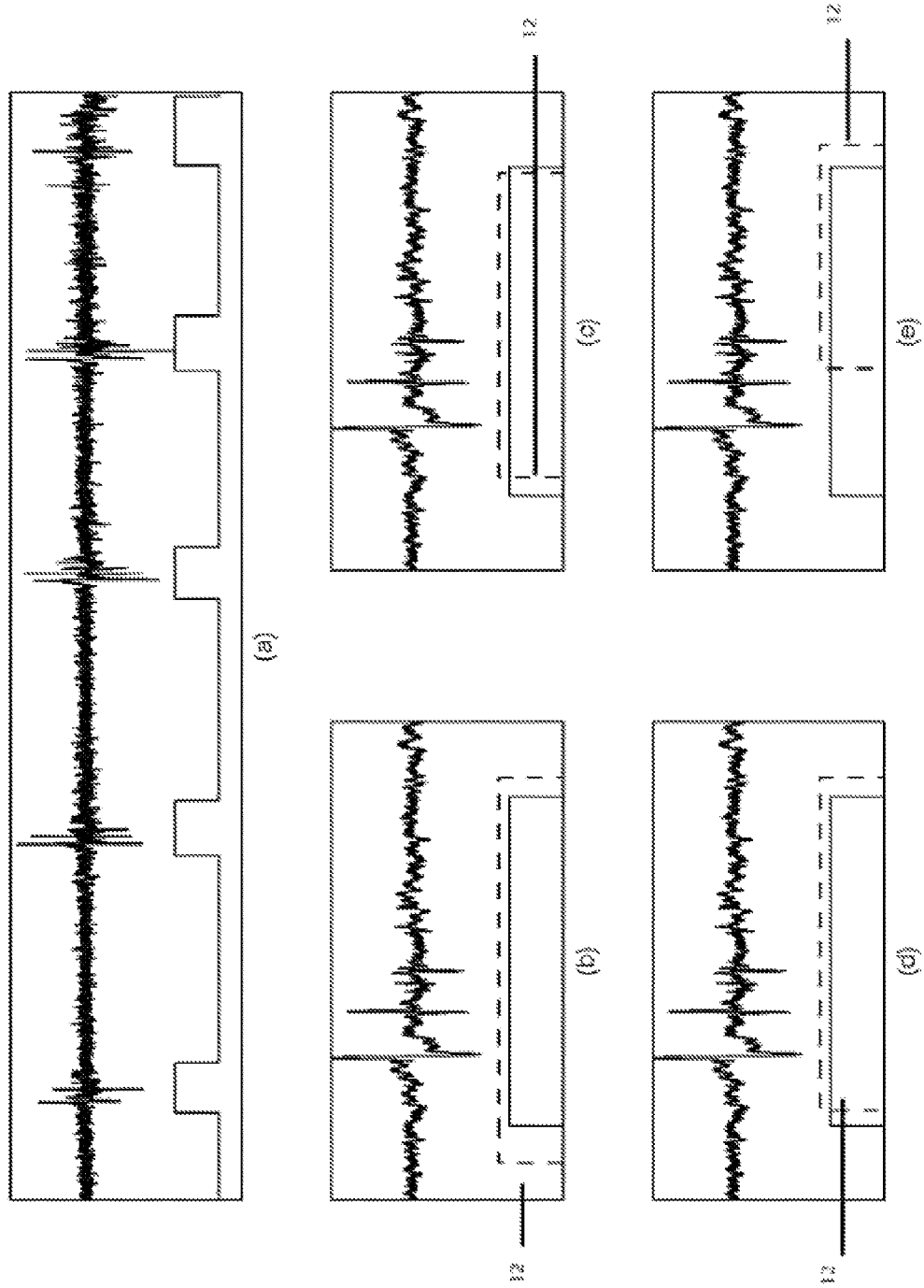
FIGS. 2 (a) – (e)

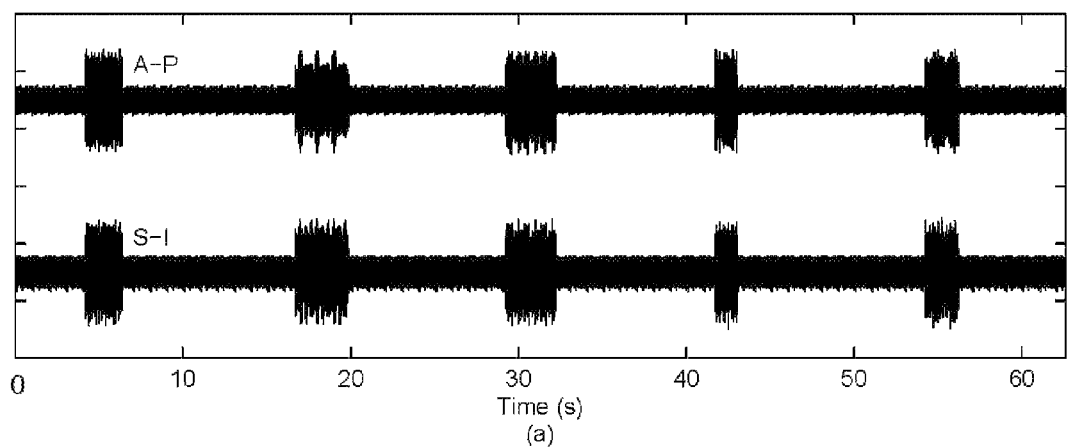
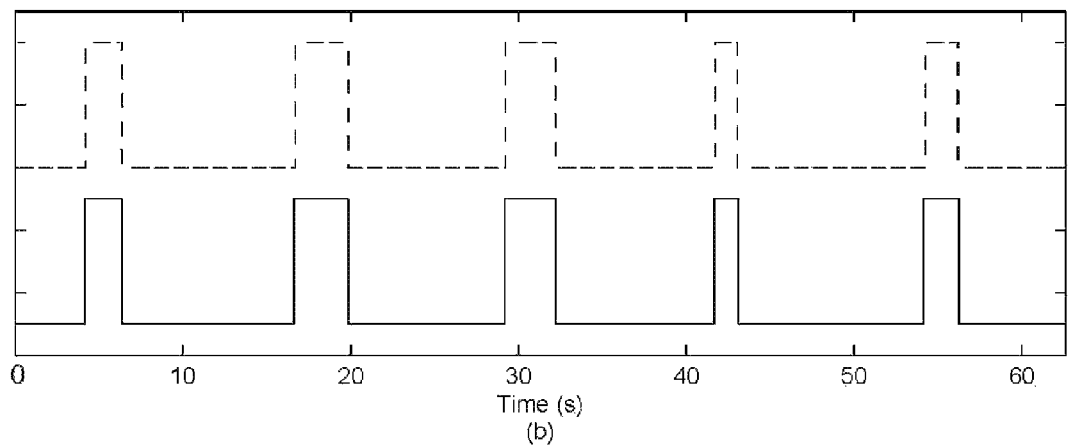
FIGs 3(a) and (b)

| Swallowing Type | TNS | CSS | % CSS | Duration (sec) | |
|---|---|---|---|---|---|
| | | | | SLP | Algorithm |
| Dry swallows | 98 | 98 | 100 | 2.4 ± 1.2 | 2.3 ± 1.4 |
| Wet swallows | 102 | 98 | 96.1 | 1.7 ± 0.6 | 2.0 ± 0.7 |
| Wet chin tuck | 95 | 83 | 87.4 | 1.9 ± 0.6 | 3.1 ± 1.2 |
| Overall | 295 | 279 | 94.6 | 2.0 ± 0.9 | 2.4 ± 1.1 |

FIG. 5

| Swallowing Type | All participants | Male | Female |
|---|---|---|---|
| Dry swallows | 2.9 ± 1.2 | 3.1 ± 1.3 | 2.8 ± 1.2 |
| Wet swallows | 2.3 ± 0.7 | 2.5 ± 0.8 | 2.2 ± 0.6 |
| Wet thin task | 3.7 ± 1.4 | 3.8 ± 1.4 | 3.6 ± 1.4 |
| Overall | 2.9 ± 1.2 | 3.0 ± 1.3 | 2.8 ± 1.2 |

FIG. 6

| Swallowing Type | BMI < 18.5 underweight | 18.5 ≤ BMI < 25 normal | 25 ≤ BMI < 30 overweight | BMI ≥ 30 obese |
|---|---|---|---|---|
| Dry swallows | 2.7 ± 1.2 | 2.9 ± 1.3 | 2.9 ± 1.2 | 3.0 ± 1.3 |
| Wet swallows | 2.3 ± 0.6 | 2.3 ± 0.7 | 2.3 ± 0.7 | 2.3 ± 0.6 |
| Wet chin tuck | 3.3 ± 0.9 | 3.4 ± 1.3 | 3.9 ± 1.5 | 4.0 ± 1.3 |
| Overall | 2.7 ± 0.9 | 2.8 ± 1.2 | 3.0 ± 1.3 | 3.0 ± 1.3 |

FIG. 7

| Swallowing Type | Age ≤ 30 | 31 ≤ Age ≤ 45 | 46 ≤ Age ≤ 60 | Age ≥ 60 |
|---|---|---|---|---|
| Dry swallows | 2.7 ± 1.1 | 2.9 ± 1.2 | 3.0 ± 1.2 | 3.2 ± 1.5 |
| Wet swallows | 2.2 ± 0.6 | 2.3 ± 0.8 | 2.3 ± 0.7 | 2.5 ± 0.6 |
| Wet chin tuck | 3.5 ± 1.2 | 3.5 ± 1.4 | 4.0 ± 1.5 | 3.8 ± 1.5 |
| Overall | 2.7 ± 1.1 | 2.9 ± 1.2 | 3.0 ± 1.3 | 3.1 ± 1.4 |

FIG. 8

METHOD AND SYSTEM OF SEGMENTATION AND TIME DURATION ANALYSIS OF DUAL-AXIS SWALLOWING ACCELEROMETRY SIGNALS

CROSS REFERENCE TO RELATED APPLICATIONS

This application claims the benefit of U.S. Provisional Patent Application No. 61/109,223 filed in the USPTO on Oct. 29, 2008.

FIELD OF INVENTION

This invention relates in general to the field of dual-axis swallowing accelerometry signals analysis and more specifically to a segmentation algorithm for performing such analysis.

BACKGROUND OF THE INVENTION

Dysphagia (swallowing difficulty) is a serious and debilitation condition that often accompanies, stroke, acquired brain injury and neurodegenerative illnesses. Individuals with dysphagia are prone to aspiration, which directly increases the risk of serious respiratory consequences, such as pneumonia. Aspiration can be defined generally as the entry of foreign material into the airway. Such foreign materials may be of many types, for example, such as foods, liquids, vomit, saliva, secretions from the mouth, or other materials.

The measurement of neck vibrations associated with deglutition is known as swallowing accelerometry, a potentially informative adjunct, to bedside screening for dysphagia. Accelerometric measurements are minimally invasive, requiring only the superficial attachment of a sensor anterior to the thyroid notch.

Recent research has forced upon exploiting this vibration signal for dysphagia screening. For example, combining accelerometry and swallowing pressure, Suryanarayanan et al. developed a hand-crafted fuzzy rule-base to classify sixteen patients with dysphagia according to aspiration risk. Additionally, from the physiological perspective, Reddy et al. attributed the accelerometric signal to the extent of laryngeal elevation during swallowing, thus arguing that accelerometry would be of diagnostic value. Furthermore, based on this premise, Das et al. proposed a hybrid fuzzy logic committee on neural networks trained to accurately distinguish between swallows from twelve healthy subjects and sixteen with dysphagia.

Moreover, studies in this area have provided further information. In a paediatric study involving children with dysphagia secondary to cerebral palsy, swallow accelerometry signals were found to be largely nonstationary, while an off-line radial basis classifier using two time-domain features differentiated between manually segmented aspiration events and safe swallows with 80% sensitivity and specificity.

Previous studies have only investigated a small number of swallows and hence the data collected was conducive to manual segmentation by a human analyst. Segmentation algorithms facilitate segmentation of larger collection of data. This is necessary as larger volumes of accelerometry data necessitate an automatic method to mitigate human error due to fatigue or oversight and to ensure consistent segmentation criteria. Such algorithms have been developed in many fields, e.g. heart sounds analysis, electroencephalogram signals analysis, knee joint vibroarthrographic signals analysis and in the analysis of urine magnetomyogran contractions during pregnancy, to name a few. In particular, several successful methods rely on multiple channels of information to enhance segmentation.

Wang and Willett have proposed a very simple algorithm that determines the number of segments automatically. This algorithm is useful but encounters a number of problems when utilized to analyze swallowing accelerometry data. Specifically, the Wang and Willett algorithm is prone to overestimating the number of segments of nonstationary variance, which is an element of swallowing accelerometry signals.

US Patent Applications No. 2005/0283096 presents another example of prior art in the area of study. The patent discloses an apparatus and method for detecting swallowing activity. The method and apparatus disclosed in this patent involve the generation of electrical signals by an accelerometer positioned on the throat of the patient and the receipt and analysis of those signals at a computing device. Gamma distribution is applied to estimate the spread and location parameters within the signals. Through the method and apparatus the type of swallowing activity undertaken may consequently be classified.

SUMMARY OF THE INVENTION

In one aspect, the present disclosure relates to a method of segmentation of dual-axis accelerometry signals, comprising: (a) generating dual-axis swallowing accelerometry signals using a sensor; (b) transferring the dual-axis swallowing accelerometry signals to a data collection means; and (c) analysing the dual-axis swallowing accelerometry signals using a segmentation algorithm applied by the data collection means; wherein the algorithm facilitates and identification of class of swallowing.

In another aspect, the present disclosure relates to a system of identifying dual-axis accelerometry signals, comprising; (a) a dual-axis sensor attached to the subject to generate signals; (b) a data collection means capable of receiving, storing and analysing swallowing data; and (c) a segmentation algorithm capable of analysing the swallowing data; wherein the signals generated by the dual-axis sensor are transferred to the data collection means as swallowing data and analysed by the segmentation algorithm; and wherein the segmentation algorithm facilitates the identical of classes of swallowing.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF DRAWINGS

The invention will be better understood and objects of the invention will become apparent when consideration is given to the following detailed description thereof. Such description makes reference to the annexed drawings wherein:

FIG. 1 is diagram showing the axes of acceleration in the anterior-posterior and superior-inferior directions.

FIG. 2(*a*) is shows a sample swallowing accelerometry signal (top) and a binary function (bottom) indicating the occurrence of swallows as pinpointed by an SLP.

FIG. 2(b) shows a sample swallowing accelerometry signal (top) and a binary function (bottom) indicating the occurrence of correctly segmented swallows where the algorithm (pulse with dashed line) slightly overestimates the swallow duration extracted by the SLP (pulse with solid line).

FIG. 2(c) shows a sample swallowing accelerometry signal (top) and a binary function (bottom) indicating the occurrence of correctly segmented swallows where the algorithm (pulse with dash line) slightly underestimates the swallowing duration extracted by the SLP (pulse with solid line).

FIG. 2(d) shows a sample swallowing accelerometry signal (top) and the binary function (bottom) indicating the occurrence of correctly segmented swallows where the algorithm (pulse with dash line) estimates the swallow duration extracted by the SLP (pulse with solid line)

FIG. 2(e) sample shows swallowing accelerometry signal (top) and binary function (bottom) indicating the occurrence of an incorrectly segmented swallow.

FIG. 3(a) is a segmentation of test signals that show a realization of the simulated signal.

FIG. 3(b) is a segmentation of test signals that show the actual indicator sequence (dash line) and the indicator sequence produced by the algorithm.

FIG. 5 is a table that shows that vibrations caused by head movement is some cases can overwhelm the vibrations of interest in the A-P direction, encumbering detection by the proposed algorithm.

FIG. 6 is a table that shows the duration of swallowing segments grouped by gender wherein an asterisk denotes a statistically significant gender difference.

FIG. 7 is a table that shows the duration of swallowing signals grouped by BMI wherein an asterisk indicates significant dependence of duration on BMI (p=0.05).

FIG. 8 is a table that shows the duration of swallowing signals grouped by age wherein and asterisk indicates significant dependence of duration on age (p=0.05)

Figure 4:
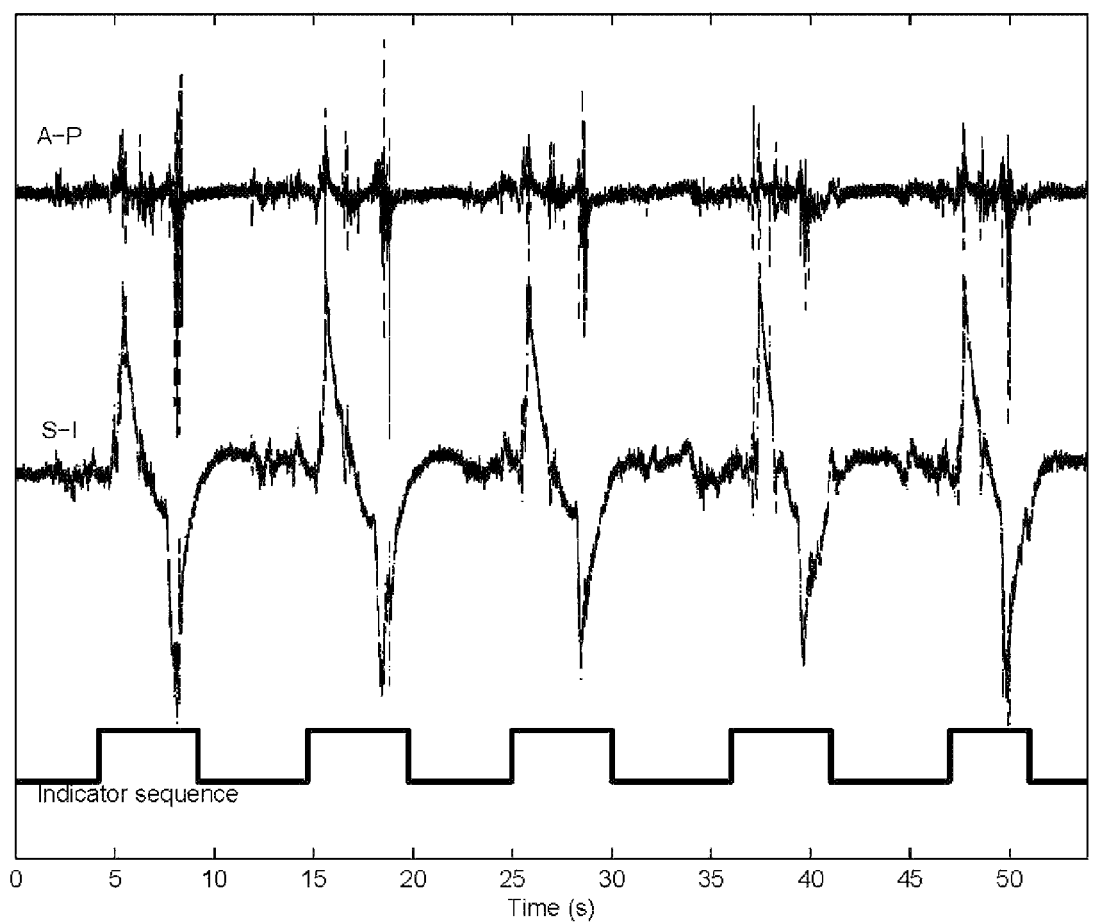
FIG. 4 shows a sample of wet chin tuck swallowing vibrations in A-P and S-I directions along with the indicator sequence obtained by the proposed algorithm.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

The proposed intention is a method and system of the segmentation of dual-axis accelerometry signals for the indication of problematic swallowing events. For example, such as dysphagia or aspiration. Swallowing events can be defined for the purpose of specific embodiments of the invention. The method and system employ a sensor and a data collection means, as well as an algorithm for analysis of the accelerometry data. The algorithm of the proposed invention may considers the stochastic properties of swallowing signals in two directions, namely anterior-posterior (A-P) and superior-inferior (S-I). The inclusion of swallowing signals in both directions may allow the algorithm to extract events associated with swallowing from the accelerometry data. Additionally, a segmentation algorithm may be applied to identify dual-axis swallowing accelerometry signals to establish the time duration of swallows.

In one embodiment of the present invention, a sequential segmentation algorithm may be applied to dual-axis swallowing accelerometry signals. Such signals may be collected through non-invasive means thus allowing for a non-invasive diagnosis of swallowing difficulties. The algorithm may be based on a piecewise fuzzy partitioning of the signal and is well-suited to long signals with nonstationary variance. In embodiments of the present invention dual-axis swallowing accelerometry signals from multiple swallowing tasks may be compared with known attributes of healthy swallows in known swallowing location. In this manner swallowing signals may be classified.

The construction of dual-axis accelerometry applied in the present invention involves collecting data from two-dimensional movement of the hyoid and the larynx during swallowing. Dual-axis accelerometry thus collects data from the hyolaryngeal complex that occurs in both anterior-posterior and superior-inferior directions during swallowing. The proposed segmentation algorithm of the present invention may involve sequential fuzzy partitioning of the signal and can be well-suited for long signals with nonstationary variance.

The method of the present invention is designed to overcome problems existing in the prior art. Previous accelerometric signal segmentation algorithms experience several hurdles. For example, known algorithms are unable to accurately analyze long signals. Specifically, the present invention offers a segmentation algorithm capable of application to long and noisy data sets. These attributes cause the present invention to be appropriate for assessments of dual-axis swallowing accelerometry, as the signals that are produced by swallowing may be of variant durations and are likely to be accompanied by noise. Furthermore, the method of present invention overcomes the hurtle of segmenting signals of nonstationary variance. Known methods and systems of the prior art are prone to overestimate number of segments for nonstationary variance signals and to experience problems with threshold tuning. The present invention overcomes each of these prior art problems.

Furthermore, generally a systematic analysis of swallowing accelerometry signals necessities the demarcation of individual swallows within an extended recorded of vibrations collected from the neck. Larger volumes of accelerometry data necessitate an automatic method, in order to mitigate human error due to fatigue or oversight and to ensure consistent segmentation criteria. In application to swallow accelerometry data the present invention may exploit both A-P and S-I vibrations for this purpose.

Additionally, the present invention offers a method and system whereby swallows may be classified in greater detail than is possible in accordance with prior art. For example, swallows may be assessed through the method and the proposed invention with respect to gender, body mass index and age. A variety of types of swallows may further be assessed through the method of the proposed invention, for example, such as, saliva swallows, water swallows in a neutral position and water swallows in a chin tuck position. These types of swallows are typically considered during a manual swallowing assessment.

Carry out the time duration analysis with respect to factors, including gender, body mass index and age, can provide a benefit as demographic and anthropometric variables may influence the duration of segmented signals. For example, males may exhibit longer swallows than females participants (p=0.05). Additionally, older persons and persons with higher body mass indices may exhibit swallows with significantly longer (p=0.05) duration than younger persons and those with lower body mass indices, respectively. The method of the present invention involves an algorithm capable of including such factors in its analysis. The algorithm of the present invention may extract individual swallows with a high accuracy rate, for example, such as over 90% accuracy.

Thus, the present invention provides several benefits over the prior art. Specifically, the algorithm of the present invention is applicable to long data sets. It is furthermore, applicable to data sets affected by noise and nonstationary variance signal data. Additionally, the method of the present invention, that involves the algorithm, permits analysis of swallowing accelerometry data.

One embodiment of the present invention includes an algorithm that functions so as to approximate locations of onsets and offsets of vibration signals over time durations, such as the vibrations of swallows. In this embodiment there may be no reason to determine the exact values of onset and offsets of new segments. Moreover, through analysis of the signals large changes in variances may be detected. In the course of this understanding the algorithms may form relationships between variables in a piecewise and stochastic manner. This may be necessary because data sets are long and the signals may be buried in noise. The algorithm may also undertake approximations regarding dual-axis swallowing accelerometry signals, for example, such as to determine maximum likelihood estimates for the mixture separation. Approximations can cut down on computational costs and allow the algorithm to function more efficiently. Using fuzzy c-means optimization of the algorithm may be able to determine time boundaries of segments, which can allow for the identification of swallowing vibrations in A-P and S-I directions. Once identified, indicator functions from both directions may be multiplied to obtain an estimate of locations and durations o signals. This step offers an advantage as noise along one of the axes can lead to an incorrect estimate of swallowing multiplicity in the corresponding signal.

Another embodiment of system of the present invention may incorporate data regarding the height, weight, body fat percentage, gender and mandibular jaw length, or other details from a person. A dual-axis accelerometer sensor may be attached to the neck of a person, anterior to the cricoid cartilage. Once the sensor is attached the person may perform a variety of swallows (e.g. water swallows with head in neutral position, or saliva swallows, etc.). Swallowing accelerometry measurement data may be collected from the sensor by a data collection means. A band-pass filtration of the data may be undertaken and the output may be stored for immediate or later analysis. The analysis may involve an application of the algorithm of the present inventions to the signal data to produce segmentation that indicates locations and durations of swallows. The analysis may further include a review of the signal results for average consistency with gender and other elements relevant to person.

The method of the present invention builds upon prior art segmentation algorithms. For example, prior art segmentation methods often consider segments of different stochastic behaviour such that a realization of a process given by N points $\{x_i | 1 \leq i \leq N\}$ can be composed of K segments with K-1 transition times $\tau = \{t_1, t_2, \ldots, t_{K-1}\}$ where $t_k \in \mathbb{Z}^+$. Furthermore, the data within the $k^{th}$ segment can be assumed to follow an independent and identically distributed Gaussian distribution with variance $\sigma_k^2$. Hence, the probability density function (PDF) for data within the $k^{th}$ segment would be given by:

$$\ln p(x_{t_{k-1}}, \ldots, x_{t_k-1} | \sigma_k^2) = -\frac{t_k - t_{k-1}}{2}\ln(2\pi\sigma_k^2) - \frac{\sum_{i=t_{k-1}}^{t_k-1} x_i}{2\sigma_k^2} \quad (1)$$

By writing $\theta = \{\sigma_1^2, \sigma_2^2, \ldots, \sigma_k^2\}$, which indicates the vector of variance for all K segments, and assuming that these segments are statistically independent, the PDF of the data set $\{x\}$ can be written as $$p(x|\tau, \theta, K) = \Pi_{k=1}^K p(x_{t_{k-1}}, \ldots, x_{t_k-1}|\sigma_k^2) \quad (2)$$

where by definition $t_0 \equiv 0$ and $t_k - 1 \equiv N$. Then, the segmentation problem demands a joint estimation of $\tau$, $\theta$ and K. The determined values would be represent the best fit of the data x to (2). Different solutions to this segmentation problem have been proposed in the literature over the years. However, computational costs associated with the proposed solutions are very high.

A second prior art segmentation algorithm is that of Wang and Willet, which is very simple algorithm, that determines the number of segments automatically and avoids threshold tuning. Wang and Willet's algorithm begins with an initial assumption that the length of any segment is bounded below by $L_{min}$ and above by $L_{max}$.

$$L_{min} \leq t_k - t_{k-1} \leq L_{max} \quad (3)$$

This assumption mandates that there is at most one change during any interval of length $L_{min}$. In other words, for $\{x_i | t_{k-1} \leq i \leq t_k + L_{min} - 1\}$ only two situations are possible and they are given by:

$x_i \sim \mathcal{N}(0, \sigma_k^2)$ for $t_{k-1} \leq i \leq t_k + L_{min} - 1$ \hfill Hypothesis 1

$\exists l_o \in [L_{min}, L_{max}]$ such that $x_i \sim \mathcal{N}(0, \sigma_k^2)$ for $t_{k-1} \leq i \leq l_o$
and $x_i \sim \mathcal{N}(0, \sigma_{k+1}^2)$ for $l_o + 1 \leq i \leq t_k + L_{min} - 1$ \hfill Hypothesis 2 where $\sigma_k^2$ and $\sigma_{k+1}^2$ are distinguishable. In other words, either the segment is homo- or heteroscedastic. The value of $l_o$, is estimated through the following relation:

$$\hat{l}_o = \text{argmax}_{l_o \in [L_{min}, L_{max}]} \left\{ \begin{array}{c} -\frac{l_o - t_{k-1}}{2}\ln(2\pi\hat{\sigma}_k^2) - \\ \frac{\sum_{i=t_{k-1}}^{l_o} x_i^2}{2\hat{\sigma}_k^2} - \\ t_k + L_{min} - \\ \frac{1 - (l_o + 1)}{2}\ln(2\pi\hat{\sigma}_{k+1}^2) - \\ \frac{\sum_{i=l_o+1}^{t_k + L_{min}-1} x_i^2}{2\hat{\sigma}_{k+1}^2} \end{array} \right\} \quad (4)$$

where $$\hat{\sigma}_k^2 = \frac{1}{l_o - t_{k-1} - 1}\sum_{i=t_{k-1}}^{l_o} x_i^2 \quad (5)$$

$$\hat{\sigma}_{k+1}^2 = \frac{1}{L_{min}}\sum_{i=l_o+1}^{l_o} x_i^2 \quad (6)$$

The data contained in the segment given $\chi = \{x_i | t_{k-1} \leq i \leq \hat{l}_o + L_{min} - 1\}$ satisfies either case 1 or case 2. In order to determine which hypothesis best describes the segment $\chi$, the minimum description length (MDL) principle is employed as follows:

$$\hat{c} = \mathrm{argmax}_{c\in[1,2]} MDL(c; \chi) = \mathrm{argmax}_{c\in[1,2]} I_c(N_x) - \frac{2c-1}{2}\ln(N_\chi) \quad (7)$$

where $N_\chi$ is the length of $\chi$ and $$I_c(N_x) = \quad (8)$$
$$\max_{\{T_1,T_2,\ldots,T_{l-1}\}\in[L_{min},L_{max}]T_0=1,T_l=N_x} \sum_{i=1}^{c} -\frac{T_i - T_{i-1}}{2}(\ln(2\pi\hat{\sigma}_i^2)+1)$$

with $\hat{\sigma}_i^2$ being the maximum likelihood (ML) estimated of variance for time interval $T\epsilon[T_{i-1}, T_i]$.

Based on the value produced by (7), a decision is reached for the given segment. This procedure continues until the entire signal is analyzed. Wang and Willet also proposed a post-hoc refinement stage to improve the accuracy of segmentation.

For simulated Gaussian time series with zero means and piecewise constant variance and lengths up to six thousand points, the algorithm reportedly performs accurately, with computation times comparable to, if not shorter than those of competing algorithms. However, for the swallowing records, which are of considerable length (>>$10^4$ points), the approximately linear complexity of the algorithm results in a marked increase in the computational time. This computation cost is further heightened when considering the two realizations of the same process (i.e., dual-axis swallowing accelerometry).

Figure 9:
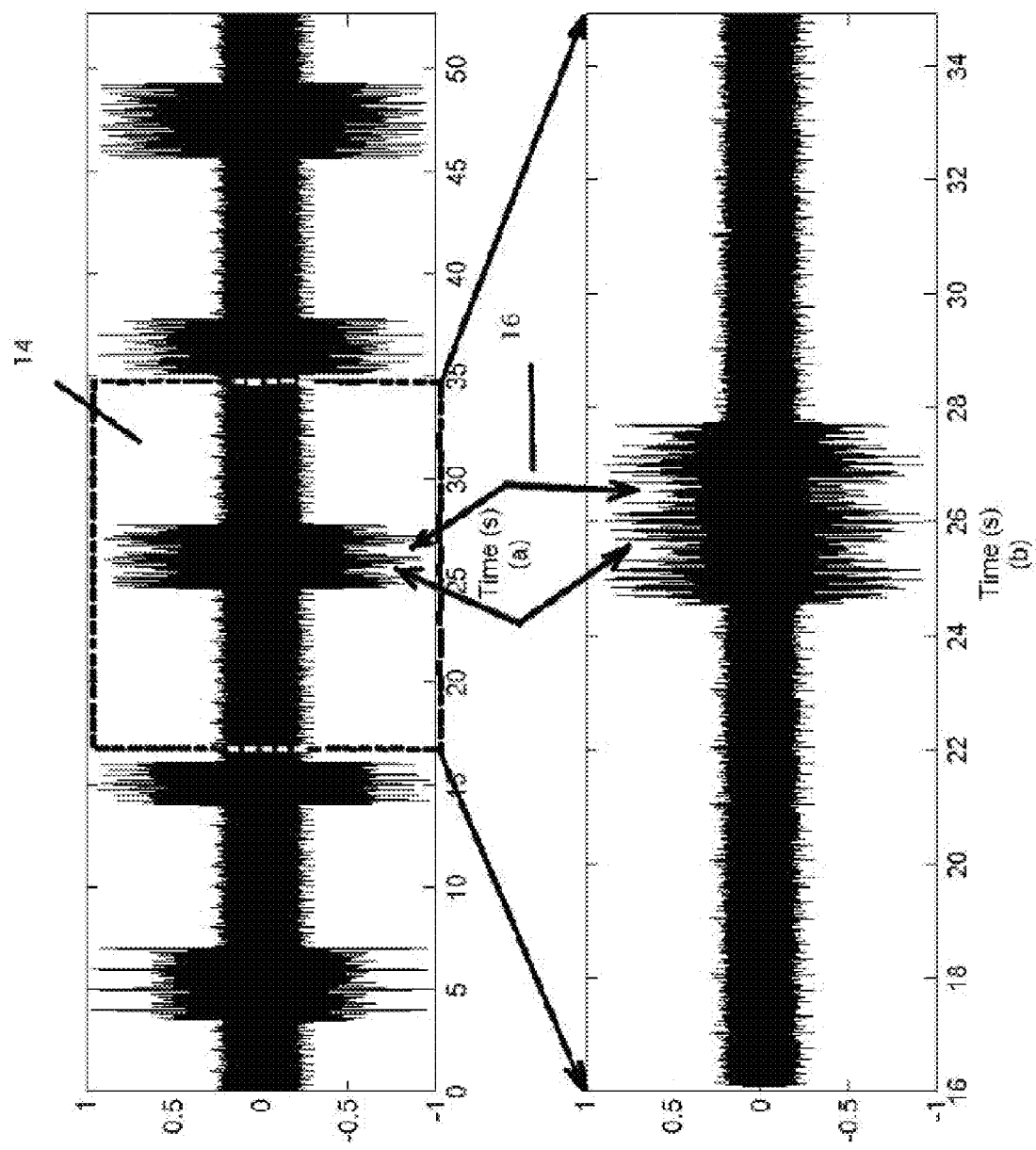
FIG. 9 is a sample realization of synthetic signal.

Swallowing accelerometry signals often possess nonstationary variance and hence the present algorithm may "overestimate" the number of segments. For example, a slight change in variance within the boundaries of a given segment would cause the algorithm to detect a transition point, when in fact the segment may be a single, cohesive swallowing event from the physiological point of view. For example, in the case of a synthetic signal as shown in FIG. 9, Wang and Willett's algorithm will correctly detect all the transition points between the baseline and the activity regions. It will also detect changes change in variances which might occur during an activity region. If the third activity region (14) is selected is selected, Wang and Willett's algorithm also detects the changes denoted by the arrows (16). While mathematically this may be correct, from a physiological point of view it is not. The present invention, therefore, may detect distinct physiological events (i.e., swallows vs. non-swallowing activity), rather than small fluctuations in variance. Embodiments of the present invention address the aforementioned challenges of lengthy dual-axis swallowing accelerometry signals.

The computational bottleneck of Wang and Willett's algorithm lies in the optimization procedures to estimate the transition point $l_o$ and the segment class, $\hat{C}$. The present invention simplifies the optimization procedures and thereby reduces the computational load. First, exact locations of the onsets and the offsets of swallow are unknown and can only be approximately determined. Hence, forcing the algorithm to determine the optimal value for $l_o$ (i.e., the exact locations of onsets and offsets) is unnecessary in the swallowing application and is not undertaken in the present invention. Secondly, the goal of the present invention regarding segmentation is not to detect small changes in variances, but rather large changes. In light of the above, the present invention involves two modified hypotheses for sequential segmentation, namely, $\phi_i \sim g_1(\phi|\theta_1)$ for $t_{k-1} \leq i \leq t_k-1$      Hypothesis 1

$\phi_i \sim g_2(\phi|\theta_2)$ for $t_{k-1} \leq i \leq t_k-1$      Hypothesis 2 where $\phi$ is a variable related to x; $g_1(\phi|\theta_1)$ and $g_2(\phi|\theta_2)$ are conditional probability density functions and $\theta_1$ and $\theta_2$ are parameter vectors. The PDF $g_1(\phi|\theta_1)$ represents the absence of swallowing activities, while $g_2(\phi|\theta_2)$ models the presence of swallowing activity.

Due to the fact that data sets are very long and the swallowing signals are buried in the noise, the relationship between $\phi$ and x is to be formed in a piecewise and stochastic manner. To follow Wang and Willett's algorithm, it is assumed that $\phi$ is a piecewise constant estimate of the variance of x. That is, choose $L\epsilon\mathbb{Z}^+$ satisfying relation (3) and $M>L$, $M\epsilon\mathbb{Z}^+$. Furthermore, it is assumed that $L<M$ in order to have $M-L$ overlap in sequential procedure. To relate the entire signal x to the variable $\phi$, the following steps are proposed:

1. Initialize $v_k=1$ and set $y=\{x_i|v_k \leq i \leq v_k+M-1\}$
2. Estimate the sample mean of y:

$$\hat{\mu}_y = E\{y\} \approx \frac{1}{M}\sum_{i=1}^{M} y_i \quad (9)$$

3. Estimate the sample standard deviation of y in a maximum likelihood (ML) sense:

$$\hat{\sigma}_y = \sqrt{\frac{1}{M}\sum_{i=1}^{M}(y_i - \hat{\mu}_y)^2} \quad (10)$$

4. Set the variable $\phi$, as follows:

$\phi_i = \hat{\sigma}_y$ for $v_k \leq i \leq v_k+M-1$      (11)

5. Set $v_{k+1}=v_k=L$ and proceed to step 2 until the entire signal is analyzed.

It can be assumed that the vector $\phi$ of standard deviations is sampled from $g_1(\phi|\theta_1)$ and $g_2(\phi|\theta_2)$ with a priori probabilities $P_1$ and $P_2$, respectively, where $0<P_1$, $P_2<1$ and $P_1+P_2=0$.

However, since these a priori probabilities are not known, it has to be assumed that $\phi$ is sampled from $p(\phi|\xi)$ which is PDF representing a mixture of $g_1(\phi|\theta_1)$ and $g_2(\phi|\theta_2)$ with mixing parameters being $P_1$ and $P_2$. In other words, $p(\phi|\xi)$ is given by $p(\phi|\xi) = P_1 g_1(\phi|\theta_1) + P_2 g_2(\phi|\theta_2)$      (12)

where $\xi = \{P_1, P_2, \theta_1, \theta_2\}$. Therefore, the mixture separation problem boils down to the estimation of the members of $\xi$. Let the set $\Phi$ drawn from $p(\phi|\xi)$ represent all possible outcomes of independent trials, then the ML estimate of would be given by $\xi^* = \mathrm{argmax}_\xi \Sigma_{\phi\in\Phi} \ln p(\phi|\xi)$.      (13)

Nevertheless, finding the maximum likelihood estimate of $\xi$ for dual-axis swallowing accelerometry signals can be computationally costly. Hence, some approximation is needed. Before proceeding further on, let's consider the available information. The location and duration (i.e. onset and offsets) of swallows are only approximately known. In addition; it is known that $\phi$ contains data which are sampled either from $g_1(\phi|\theta_1)$ and $g_2(\phi|\theta_2)$ depending on whether or not a swallow occurred. Therefore, rather than solving (13), only indicator functions defined as:

$$u_{g_1}(\phi_i) = \begin{cases} \kappa & \phi_i \sim g_1(\phi|\theta_1) \\ 0 & \text{otherwise} \end{cases} \quad (14)$$

$$u_{g_2}(\phi_i) = \begin{cases} 1-\kappa & \phi_i \sim g_2(\phi|\theta_2) \\ 0 & \text{otherwise} \end{cases} \quad (15)$$

can be formed, where $0 \leq K \leq 1$. It is clear that $u_{g_1} + u_{g_2} = 1$. The functions introduced by (14) and (15) indicate the presence of different segments (i.e. no-swallow or swallow), but the functions do not reveal any information about the time boundaries of these segments. Therefore, the next step is to determine these boundaries. Let us write the two indicator functions as a matrix $U = [u_{g_1}, u_{g_2}]$. Furthermore, the segment space is the set $$S_\phi = \{U \in V_U | u_{g_1}, u_{g_2} \in [0,1]; u_{d_1} + u_{d_2} = 1; 0 < \Sigma_{i=1}^N u_{g_{ji}} < N, f \text{ or } j = 1, 2\} \quad (16)$$

where $u_{g_{ji}} = u_{g_j}(\phi_i)$ and $V_U$ is the vector space of U. To find these segments, i.e. the regions representing when $\phi$ was sampled from either distribution, an objective function $J_m(U, v) : S_\phi \times \mathbb{R}^+$ should be minimized:

$$J_m(U,v) = \Sigma_{i=1}^N \Sigma_{j=1}^2 (u_{g_{ji}})^m (d_{ji})^2 \quad (17)$$

where $$(d_{ji})^2 = \|\phi_i - v_j\|^2 \quad (18)$$

is the inner product induced norm; $v_j$ is the prototype of $u_{g_j}$, $j=1, 2$; and m is the weighting exponent given by $m \in [1, \infty]$. For the purposes of the present invention, m=2. However, it should be noted that $J_m(U, v)$ can only by minimized if $d_{ji} > 0$ for $\{j, i | 1 \leq j \leq 2, 1 \leq i \leq N\}$, m>1 and $u_{g_j}$, $v_j$ are obtained through the following iterative steps:

$$u_{g_{jk}} = \left[\sum_{o=1}^2 \left(\frac{d_{jk}}{d_{ok}}\right)^{2/(m-1)}\right]^{-1} \quad (19)$$

$$v_j = \frac{\sum_{k=1}^N (u_{g_{jk}})^m \phi_k}{\sum_{k=1}^N (u_{g_{jk}})^m} \text{ for } j = 1, 2. \quad (20)$$

The above formulation is a 2-class fuzzy c-means optimization problem. Furthermore, this minimization can be simply realized through Picard iteration of (19) and (20):

1. Randomly initialized $U_{(0)} \in S_\phi$ and then at steps h=1, 2 . . .
2. Calculate $\{v_j^{(h)}\}$ with (20) and $U^{(h-1)}$
3. Compute $U^{(h)}$ using $\{v_j^{(h)}\}$ and (19)
4. If $\|U^{(h)} - U^{(h-1)}\| \leq \epsilon$ stop, otherwise, increment h and return to step 2.

The aforementioned steps yield two indicator functions: $u_{g_1}$ and $u_{g_2}$ which denote the absence or presence of swallowing on one axis. For the dual-axis recordings, there are four indicator functions: $u_{g_1AP}$, $u_{g_2AP}$, $u_{g_1SI}$ and $u_{g_2SI}$ with $u_{g_2AP}$ and $u_{g_2SI}$ representing independently the absence or presence of swallowing vibrations in the A-P and S-I directions, respectively. However, excessive noise along one of the axes may lead to an incorrect estimate of swallow multiplicity in the corresponding signal. Therefore, to obtain a more accurate estimate of the locations and durations of swallows, the indicator functions from both axes should be multiplied. Therefore, the dual-axis indicator function, $u_{DA}$ is given by:

$$u_{DA} = u_{g_2AP} \times u_{g_2AP} = \begin{cases} \rho & \phi \sim g_2(\phi|\theta) \\ 0 & \text{otherwise} \end{cases} \quad (21)$$

where $0 << \rho \leq 1$. If desired, $u_{DA}$ can be turned into binary indicator sequence as:

$$u_{DA} = \begin{cases} 1 & \rho \geq \gamma \\ 0 & \text{otherwise} \end{cases} \quad (22)$$

where $\gamma$ is predetermined threshold value. The algorithm of the present invention is intended to be applicable to very long and noisy data sets.

The system of the present invention may include an accelerometer sensor capable of producing signals indicating swallowing activities. A person skilled in the art will recognize that a variety of accelerometer sensors may be utilized. In one embodiment of the present invention a dual-axis accelerometer, for example, such as an ADXL322 or other analog device, may be applied. The sensor may be attached to a person's neck. The sensor should be positioned anterior to the cricoid cartilage of the person's neck. A variety of means may be applied to position the sensor and to hold the sensor in such position, for example, such as double-sided tape. The positioning of the sensor should be such that the axes of acceleration are aligned to the anterior-posterior and super-inferior directions 10, as shown in FIG. 1.

In another embodiment of the present invention, details may be collected from the person, such as height, weight, body fat percentage, gender and mandibular jaw length, or other details. The person may be required to perform a variety of types and swallows (e.g. water swallow with head in neutral position, or saliva swallows, etc.). For each swallow, swallowing accelerometry measurement data may be generated by the sensor.

Signals generated by the sensor may be passed as data to a band-pass filter hardware. A person skilled in the art will recognize that a variety of filters may be applied, such as a filter with a pass band of 0.1-3000 Hz. Once filtered the signal data may be sampled, for example, such as at 10 kHz using LabVIEW program running on a laptop computer. A person skilled in the art will recognize that other sampling techniques may be applied, including other software programs and computer hardware. Additionally, data storage means may be included, either on-site or remotely. Signal data may be stored in such data storage means for subsequent off-line analysis. Such as analysis will be performed by way of the algorithm of the present invention which must be stored on the computer hardware and compatible with the software of the system of the present invention.

EXAMPLE 1

The accuracy of the segmentation algorithm of the present invention has been evaluated in the course of a study which undertook two evaluations. First, by way of a set of simulated test signals with known change points, i.e. swallow locations;

and secondly, by way of a subset of signals with 295 real swallows manually extracted by speech language pathologist (SLP).

Data Collection

Four hundred and eight (408) participants (aged 18-65) were recruited over a three month period from a public science centre. Participants had no documented swallowing disorders and passed an oral mechanism exam prior to participation.

Participants sat behind a screen for privacy. They answered a set of questions relating to medical and swallowing history. A speech language pathologist measured the height, weight, body fat percentage (BIA Meter, BC-500, Tanita) and mandibular jaw length of each participant. A dual-axis accelerometer (ADXL322, Analog Device) was attached to the participant's neck (anterior to the cricoid cartilage) using double sided tape. The axes of acceleration were aligned to the anterior-posterior and superior—inferior directions, as show in FIG. 1. Data were band-pass filtered in hardware with a pass band of 0.1-3000 Hz and sampled at 10 kHz using a custom LabVIEW program running on a laptop computer. Data were saved for subsequent off-line analysis.

With the accelerometer attached, each participant was cued to perform five saliva swallows. After each swallow, there was a brief rest to allow for saliva production. Subsequently, the participant completed five water swallows by cup with their chin in neutral position (i.e. perpendicular to the floor) and five water swallows in the chin-tucked position. Water was served chilled, in ten individual cups so that pre and post swallowing cup weight could be measured on a digital scale. The measurements facilitated the estimation of bolus volume. Previous research suggested that natural sip size during this kind of task is between 5 an 8 ML per sip. The entire data collection session lasted fifteen minutes per participant.

Examination of the collected data revealed that some acquired signals were inadequate for further analysis due to the presence of strong disturbances, such as vocalization, coughing, and excessive head movements. Nevertheless, 9800 swallows were retained for subsequent analysis.

Validation with Synthetic Test Signals

In the collected data, exact locations of swallow onsets and offsets were unknown as corresponding videofluoroscopic sequences were not acquired. The synthetic signals with known change points thus provided a gold standard against which the segmentation algorithm could be benchmarked.

To ensure that the test signals mimicked the dual-axis swallowing accelerometry signals acquired in this experiment, the following data generation rules applied.

For every realization, two signals should be generated: one simulating acceleration in the A-P direction, and the other simulating acceleration in S-I direction.

There should be five distinct intervals where the variance of signals increases above the baseline variance.

Each of the five intervals should have random duration and random frequency components to mimic intersubject variations.

The following definitions of a signal $S_j(n)$ adheres to the above rules.

$$s_j(n) = \begin{cases} \sum_{l=1}^{15} b_{jl}\sin(2\pi f_{jl}nT + \theta_l) + \\ \sum_{w=1}^{4} 0.2\sin(2\pi f_{jw}nT) & n_1 \leq n \leq n_2 \\ \sum_{l=1}^{15} b_{jl}\sin(2\pi f_{jl}nT + \theta_l) + \\ \sum_{w=1}^{4} 0.2\sin(2\pi f_{jw}nT) & n_3 \leq n \leq n_4 \\ \sum_{l=1}^{15} b_{jl}\sin(2\pi f_{jl}nT + \theta_l) + \\ \sum_{w=1}^{4} 0.2\sin(2\pi f_{jw}nT) & n_5 \leq n \leq n_6 \\ \sum_{l=1}^{15} b_{jl}\sin(2\pi f_{jl}nT + \theta_l) + \\ \sum_{w=1}^{4} 0.2\sin(2\pi f_{jw}nT) & n_7 \leq n \leq n_8 \\ \sum_{l=1}^{15} b_{jl}\sin(2\pi f_{jl}nT + \theta_l) + \\ \sum_{w=1}^{4} 0.2\sin(2\pi f_{jw}nT) & n_9 \leq n \leq n_{10} \\ \sum_{l=1}^{15} b_{jl}\sin(2\pi f_{jl}nT + \theta_l) + \\ \sum_{w=1}^{4} 0.2\sin(2\pi f_{jw}nT) & \text{otherwise} \end{cases} \quad (23)$$

where $j=1, 2$ indexes the two directions; $T=0.0001$ seconds; $1 \leq n \leq N$ and $N \sim \mathcal{N}(600000, (50000)^2)$ with a constraint that $N > 150000$; $N > n_{10} > n_9 > \ldots > n_1$; $|n_{2q}-n_{2q-1}| \sim \mathcal{N}(250000, (5000)^2)$ for $1 \leq q \leq 5$ with a constraint that $|n_{2q}-n_q| > 5000$; $n_{2\kappa+1}-n_{2\kappa-1}=\lfloor N/5 \rfloor$ where $1 \leq \kappa \leq 4$; $b_{jl}$ is uniformly drawn from $[0, 0.05]$; $f_{jl}$ is uniformly drawn from $[1,5000]$; $\theta_l$ is uniformly drawn from $[0, \pi]$ and $f_{jw} \sim \mathcal{N}(90, (15)^2)$ with a constraint $f_{jw} > 1$. Using the above definition, one thousand (1000) pairs of dual-axes test signals were simulated. The top graph of FIG. 3 depicts a typical simulated test signal.

Accuracy was defined as a number of correctly identified high-variances segments divided by the number of all high-variance segments. To be considered correct, an extracted segment had to overlap with the corresponding known segment by at least 90%.

Validation Against Manually Segmented Swallows

As a second evaluation step, a speech pathologist (SLP) manually segmented nineteen recordings representing saliva swallows (dry swallows), twenty recordings representing water swallows (wet swallows), and nineteen recordings representing water swallows in the chin-tuck position (wet chin tuck). Manual segmentation involved the location of onset and offsets by visual inspection and auditory verification. Each recording contained five or six swallows, yielding a total of 295 swallows. It should be noted that the selected recordings were chosen to fairly represent different age and gender groups of the population under study.

In the validation against the human expert, a correctly segmented swallow was defined for the purpose of the study as one in which there was a minimum 90% overlap with the SLP extracted swallow. A sample swallowing accelerometry signal is depicted in FIG. 2(a) along with a binary indicator function, where "high" denoted the presence of a swallow as indicated by the SLP. The second swallow is arbitrarily selected in FIG. 2(b)-(e) to illustrate different segmentation possibilities. In each graph, the dashed lines represent possible indicator functions obtained by the algorithm 12. Evidently, to be considered a correctly segmented swallow as in graphs (b)-(d), most of the swallow duration (>90%) as indicated by the SLP must be captured. Otherwise, the algorithm is deemed to have incorrectly identified the swallow; as exemplified in FIG. 2(e).

After signals from all 408 participants had been segmented, non-parametric inferential statistical methods and linear regression analysis were used to test for potential effects of gender, BMI and age on swallowing duration.

Results

With the 1000 pairs of simulated test signals, the extraction accuracy of the proposed algorithm was 97.7±1.3%. Also, the average duration of the extracted segment was $(2.59 \pm 0.50) \times 10^4$ points which is statistically similar (p=0.18) to the average duration of the original segments ($2.5 \times 10^4$ points). This close agreement between original and extracted segment onsets, offsets and durations is illustrated in the bottom graph of FIG. 3. Results with the test signals demonstrated that the proposed algorithm is indeed capable of accurately extracting segments with elevated variance and varying length from long time series.

The results of the validation against manual segmentation by the SLP are summarized in FIG. 5. Each row in the table represents the performance of the segmentation algorithm on one type of swallow.

Evidently, the proposed algorithm achieves very good overall accuracy considering that the segmentation in performed on raw data (i.e. there was no pre-processing of data). The lowest accuracy is achieved for wet chin tuck swallows. However, this is expected since the wet chin tuck swallows are manifested through very complex signals, especially in the S-I direction, as shown in FIG. 5.

The temporal accuracy of the algorithm can be examined through a comparison of the durations of manually and automatically segmented swallows. The average durations are shown in the last two columns of FIG. 5. Several observations are in order. While, the durations for dry the wet swallows appear to agree closely with the durations obtained by the SLP, a Wilcoxon rank-sum test revealed that the durations are statistically similar only for the dry swallows (p=1.10). The durations of the wet chin tuck swallows were overestimated by the algorithm, on average, by one second. The overestimation was due to the overwhelming motion artefact depicted in FIG. 4.

With additional measurements, e.g., a head motion sensor; these swallow durations could be further refined. Additionally, the segmented vibration signals likely included events associated with both the oral and pharyngeal phase of swallowing, each of which persists for approximately one second. This would explain the algorithm's overall average duration of 2.4±1.1 s in FIG. 5, which incidentally, is consistent with the temporal characterizations of the oral-pharyngeal phase of swallowing reported by Sonies et al.

Analysis of Swallowing Signals' Duration

The study further attempted to uncover any associations between the duration of the segmented signals and the anthropometric/demographic variables, namely, gender, BMI or age. The results of such an analysis are summarized in Tables 2-4. The table entries are average durations of the segmented signals in seconds for different levels of the selected variables (gender, BMI or age). While both neck circumference and BMI were measured, a simple linear regression analysis showed these variables were highly correlated. Therefore, neck circumference was discarded and BMI was chosen for further analysis. The latter variable is appealing since participants can be grouped according to standardized BMI intervals.

In FIG. 6, events associated with wet swallows are shown as consistently manifested as the shortest signals (Wilcoxon rank-sum test, $p \ll 10^{-5}$), while the events associated with wet chin tuck swallows tend to embody the longest signals (Wilcoxon rank-sum test, $p \ll 10^{-5}$). The extended length of the wet chin tuck swallows has already been attributed to the algorithm's overestimation in the presence of excessive motion artefact. Regarding the other types of swallows, Sonies et al. also found that wet swallows were shorter than dry ones. Finally, the swallowing signals obtained from male participants were longer than those extracted from female participants, for dry and wet swallow types (Wilcoxon rank-sum test, $p \ll 10^{-5}$). This difference in duration can be attributed to gender-based anatomical differences in the oropharyngeal mechanism. The gender difference did not appear in the wet chin-tuck swallows due to inflated variability in durations for this task, likely due to motion artefact.

Data reflected in FIG. 7 suggests that as a person's BMI increases, the duration of the swallowing events increases as well. According to a regression test, this dependence on BMI is statistically significant for the events associated with wet chin tuck swallows ($p < 10^{-5}$). A possible expectation is that an increase in adipose tissue results in an attenuation of the signal amplitude and velocity. The latter effect may allow the vibration signal to decay more slowly, thereby extending the duration of the measured activity.

Moreover, the results suggest that as the age of the participant increases, the duration events associated with a swallow tends to increase as well (FIG. 8). Based on the results of a regression test, this dependence on age is statistically significant for the events associated with all types of swallows ($p \ll 10^{-5}$). This can trend may be attributed to the age-related decoupling of oral and pharyngeal stages of swallowing, leading to longer overall swallowing times, It will be appreciate by those skilled in the art that other variations of the embodiments described herein may also be practiced without departing from the scope of the invention. Other modifications are therefore possible. For example, the system may be applied to the collection of other signal data that involves long data sets that include a clear activation period that has a significantly different variance from the baseline, such as upper limb movement in patients after strokes, automatic step detection and extraction of movements while a person is washing his or her face. A skilled reader will understand that other data may also be utilized in embodiments of the present invention. Moreover, the present invention may be applied to three-dimensional data reflecting a phenomenon that manifests itself in the same manner in all three dimensions.

What is claimed is:

1. A method for segmentation and analysis of dual-axis accelerometry signals for the indication of problematic swallowing events comprising the following steps:
   a. providing an accelerometer proximate to a swallowing location for detecting dual-axis movements and respective time durations for said detected dual-axis movements and for generating dual-axis accelerometry signals having onsets and offsets;

b. transmitting said generated dual-axis accelerometry signals to a data storage device for storage;

c. analyzing the generated dual-axis accelerometry signals to determine swallowing segments and non-swallowing segments;

d. identifying a set of swallowing signals from the generated dual-axis accelerometry signals;

e. comparing said set of swallowing signals with known attributes of healthy swallowing; and, f. identifying a subset of problematic swallows wherein step c includes implementing a sequential segmentation algorithm using fuzzy c-means optimization;

wherein step d includes identification of anterior-posterior (A-P) direction vibrations and superior-inferior (S-I) direction vibrations comprising the set of swallowing signals;

wherein the implementation of the algorithm includes the steps of:

i. forming a first indicator function for a non-swallowing segment in said A-P direction;

ii. forming a second indicator function for a swallowing segment in the A-P direction;

iii. forming a first indicator function for a non-swallowing segment in the S-I direction;

iv. forming a second indicator function for a swallowing segment in the S-I direction;

v. applying said fuzzy c-means optimization for determining the time boundaries for each of said swallowing and non-swallowing segments;

vi. multiplying said first indicator function in the A-P direction by said first indicator function in the S-I direction for noise reduction; and, vii. multiplying said second indicator function in the A-P direction by said second indicator function in the S-I direction for noise reduction.

2. The method of claim 1 wherein said algorithm approximates locations of said onsets and said offsets over said respective time durations by detecting large changes in signal variance.

3. The method of claim 1 wherein steps c to f inclusive include the step of using a computer for analyzing, identifying, comparing and identifying respectively.

4. The method of claim 1 further comprising the step of classifying the set of swallowing signals by patient demographics and anthropometrics.

5. The method of claim 1 further comprising the step of classifying the set of swallowing signals by a type of swallowing wherein said type of swallow includes one of the following types: saliva swallow, water swallow in a neutral position, and water swallow in a chin tuck position.

6. The method of claim 1, wherein step b further includes the step of band-pass filtration for noise reduction.

7. A system for segmentation and analysis of dual-axis accelerometry signals for the indication of problematic swallowing events, said system comprising:

a. a sensor adapted to be placed proximate to a known swallowing location for detecting dual-axis vibrations compromising vibrations on an anterior-posterior axis (A-P direction) and vibrations on a superior-inferior (S-I direction) axis and generating dual-axis accelerometry signals;

b. data storage means for receiving and a storing said generated dual-axis accelerometry signals;

c. data processing means for identifying a set of swallowing and non-swallowing events from the generated dual-axis accelerometry signals and determining the duration of individual swallowing events;

d. means for identifying a subset of problematic swallowing events from said set;

e. wherein said data processing means comprises means for sequential segmentation of the data comprising;

i. means for forming a first indicator function for a non-swallowing segment in said A-P direction;

ii. means for forming a second indicator function for a swallowing segment in the A-P direction;

iii. means for forming a first indicator function for a non-swallowing segment in the S-I direction;

iv. means for forming a second indicator function for a swallowing segment in the S-I direction;

v. fuzzy c-means optimization for determining the time boundaries for each of said swallowing and non-swallowing segment;

vi. means for multiplying said first indicator function in the A-P direction by said first indicator function in the S-I direction for noise reduction; and vii. means for multiplying a second indicator function in the A-P direction by said second indicator function in the S-I direction for noise reduction;

viii. wherein the results are an accurate estimate of the location and duration of swallows.

8. The system of claim 7 further comprising a comparator for comparing an attribute of said swallows against the known attributes healthy swallows.

9. The system of claim 8 further comprising a noise filter between the sensor and the data storage means.

10. The system of claim 9 further comprising means for incorporating anthropometric and demographic data to the data processing means for categorizing the dual-axis accelerometry data.

11. The system of claim 10 further comprising means for incorporating a plurality of swallow descriptions for further characterizing the dual-axis accelerometry data.

* * * * *